(12) United States Patent
Mann et al.

(10) Patent No.: US 6,881,850 B2
(45) Date of Patent: Apr. 19, 2005

(54) HETEROCYCLICALLY ANNELLATED INDENOCHROMENE DERIVATIVES

(75) Inventors: Claudia Mann, Munich (DE); Manfred Melzig, Wessling (DE); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 0 days.

(21) Appl. No.: 10/720,442

(22) Filed: Nov. 25, 2003

(65) Prior Publication Data

US 2004/0092743 A1 May 13, 2004

Related U.S. Application Data

(62) Division of application No. 09/889,025, filed as application No. PCT/EP00/11078 on Nov. 9, 2000, now Pat. No. 6,660,727.

(30) Foreign Application Priority Data

Nov. 10, 1999 (DE) .......................... 199 54 170
Nov. 11, 1999 (DE) .......................... 199 54 435

(51) Int. Cl.[7] ................. C07D 311/78; C07D 311/94; C07D 311/96; A61K 31/33; A61K 31/35
(52) U.S. Cl. ................. 549/382; 549/41; 549/381; 549/432; 514/183; 514/453; 514/468
(58) Field of Search ................. 549/382, 41, 381, 549/432; 514/183, 453, 468

(56) References Cited

U.S. PATENT DOCUMENTS

| | | | |
|---|---|---|---|
| 3,567,605 A | 3/1971 | Becker | 204/158 |
| 5,349,065 A * | 9/1994 | Tanaka et al. | 546/15 |
| 5,631,720 A | 5/1997 | Guglielmetti et al. | 351/162 |
| 5,645,767 A | 7/1997 | Gemert | 252/586 |
| 5,698,141 A | 12/1997 | Kumar | 252/586 |
| 5,723,072 A | 3/1998 | Kumar | 252/586 |
| 5,869,658 A * | 2/1999 | Lin et al. | 544/106 |
| 5,961,892 A | 10/1999 | Gemert et al. | 252/586 |

FOREIGN PATENT DOCUMENTS

| | | |
|---|---|---|
| DE | 199 02 771 | 12/1999 |
| EP | 0 987 260 | 5/1999 |
| WO | 97/48762 | 12/1997 |
| WO | 98/28289 | 7/1998 |
| WO | 99/15518 | 4/1999 |
| WO | 99/23071 | 5/1999 |

* cited by examiner

Primary Examiner—Ba K. Trinh
(74) Attorney, Agent, or Firm—Crowell & Moring LLP

(57) ABSTRACT

The present invention relates to specific photochromic heterocyclically annellated indenochromene derivatives and the use thereof in plastics of all types, particularly for ophthalmic applications. In particular, the present invention relates to indeno[1,2-h]chromene derivatives having the following general formula (I) and indeno[2,1-f]chromene derivatives having the following general formula (II):

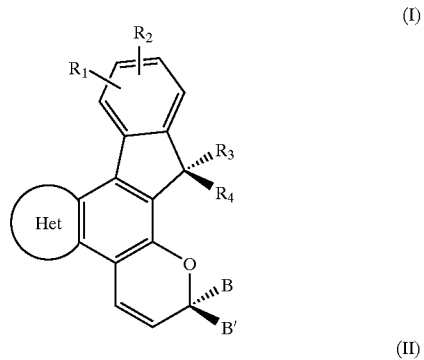

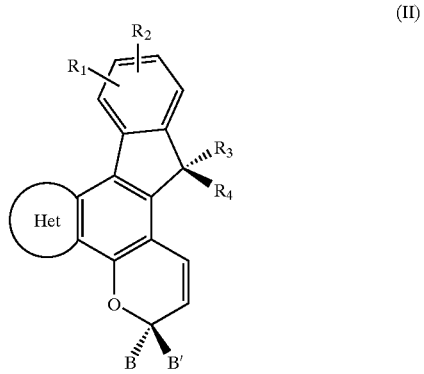

6 Claims, 3 Drawing Sheets

HETEROCYCLICALLY ANNELLATED INDENOCHROMENE DERIVATIVES

SPECIFICATION

Figure 1:
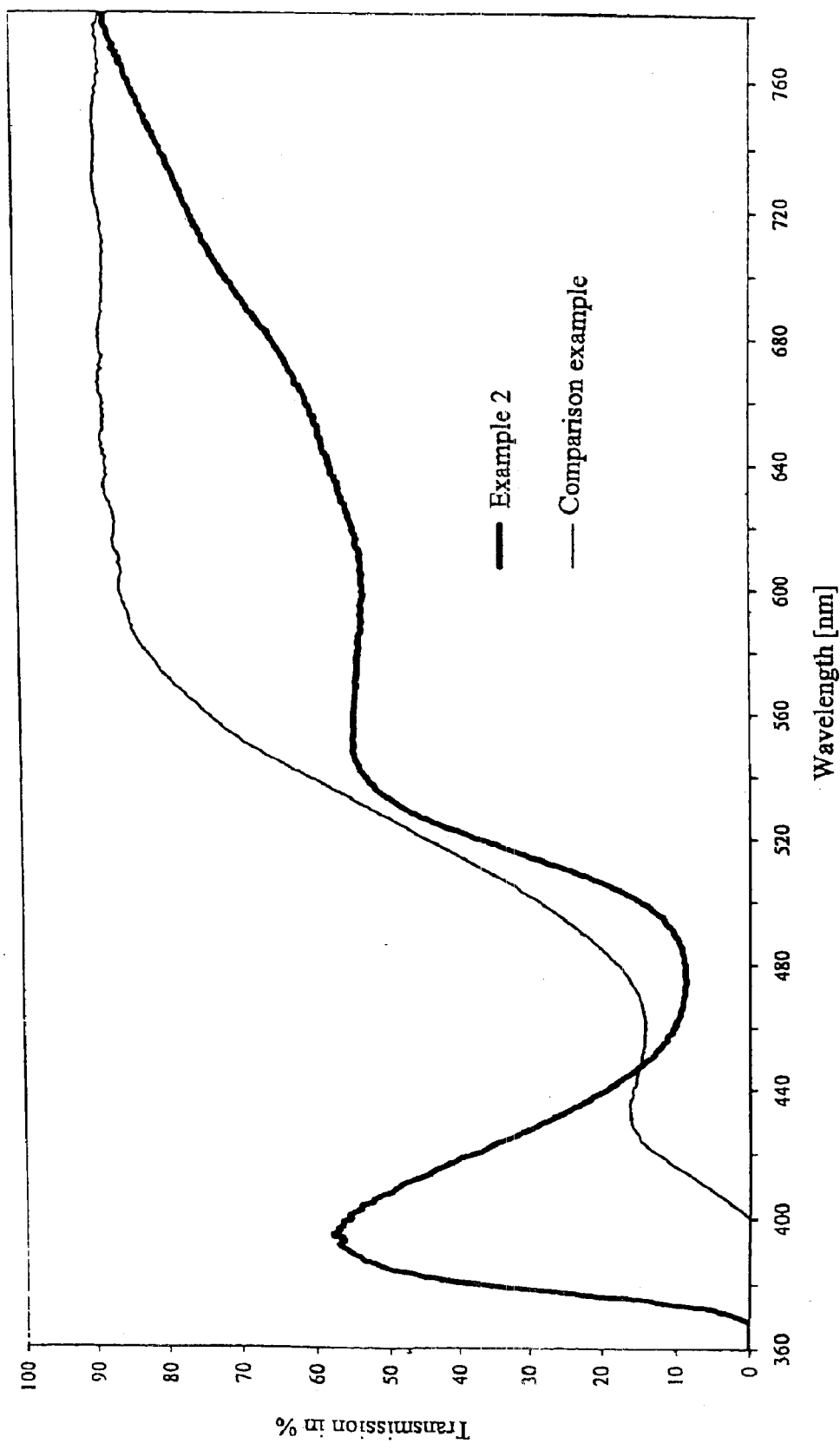

The present invention relates to photochromic indenochromene derivatives and the use thereof in plastics of all types, particularly for ophthalmic applications. In particular, the present invention relates to specific photochromic heterocyclically annellated indeno[2,1-f] chromene derivatives and specific photochromic,\ heterocyclically annellated indeno[1,2-h]chromene derivatives.

There are various known classes of dyes that reversibly change their color when irradiated with light of certain wavelengths, particularly sun light. This is due to the fact that these dye molecules change into an excited colored state when supplied with energy in the form of light. They leave this state again when the energy supply is interrupted, and thereby return to their colorless or at least their hardly colored normal state. These photochromic dyes include, for instance, naphthopyrans with various substituents, which have previously been described in the prior art.

Pyrans, especially naphthopyrans and larger ring systems derived therefrom, are photochromic compounds, which to this day continue to be the subject of intensive research. Although a first patent application (U.S. Pat. No. 3,567,605) was filed as early as 1966, it was not until the nineties that compounds, which appeared suitable for the use in eyeglasses, were developed.

Heterocyclically annellated benzopyrans are known, for instance, from U.S. Pat. No. 5,631,720. Relatively minor structural changes in the heterocycle have an enormous influence on the lightening rate (a factor of about 5). The compounds described in U.S. Pat. No. 5,631,720, however, have the drawback that they only cover the range from about 430 to 450 nm (absorption maximum of the excited form), i.e., only orange to red tints may be obtained.

WO 98/28289 describes compounds that supply dull red to red-violet tints, but the bathochromic effect of the substitution compared to 2 methyl groups is low at 25 nm. The influence on the lightening kinetics is negative, with the lightening rate being slightly retarded in all cases. The specified structure allows only substitutions that have hardly any effect on the lightening rate. Fluoreno- and naphthopyrans, which provide red-violet to green tints are known, for instance, from WO 99/15518 and DE 198 24 278 or DE 199 02 771. They are distinguished by their excellent long-term stability and good temperature stability (little dependence of the darkening depth on the temperature). The possible substitutions described therein, however, allow comparatively little latitude with respect to the lightening rate.

The introduction of a heterocyclic component by replacing the central C atom of the fluorene structure by N—R as proposed in WO 99/23071 results in compounds whose absorption maximum in the non-excited state is around or above 400 nm, i.e., clearly within the visible range. However, since the absorption extends beyond the maximum far into the violet and blue spectral region, compounds with a strong yellow tint in their non-excited state are obtained. They are therefore not suitable for use in eyeglasses.

Likewise disadvantageous is the introduction of a heterocyclic unit on the two benzene rings of the indenonaphthopyran structure as described in U.S. Pat. No. 5,698,141 and U.S. Pat. No. 5,723,072. The darkening depth of these compounds (usually given as colorability $A_0$) is low compared to the compounds of U.S. Pat. No. 5,631,720. In addition, compounds with very many annellated rings are obtained, which for the most part clearly absorb in the visible range in their non-excited state, i.e., the compounds are yellow in their non-excited state. Insofar as the compounds in their excited state show an absorption maximum in the range of 576–600 nm, i.e., a blue excitation color, green compounds are obtained, which are generally not very suitable for use in eyeglasses.

U.S. Pat. No. 5,645,767 and U.S. Pat. No. 5,869,658 describe the positive effect on the photochromic properties of indeno fusing to the f-side of the naphthopyran system. The compounds generally show longer wave absorption and increased darkening performance. EP-A-0 987 260 and DE 199 30 290 describe systems in which the indene unit is integrated in a spiro structure. These compounds are distinguished by excellent durability and rapid lightening rates with simultaneous good darkening performance.

The darkening tint of the aforementioned systems described in the prior art depends primarily on the substituents at the 3-position in 3H-naphtho[2,1-b] pyrans or, on the substituents at the 2-position in 2H-naphtho[1,2-b] pyrans. For technical applications, cosmetically neutral darkening tints, such as brown or gray, are preferred. The aforementioned compound systems have strong tints, however, so that only mixtures of different dyes can be used.

Thus, the object of the present invention is to provide novel photochromic systems, which, in contrast to the compounds thus far available in the prior art, should have broader absorption bands for duller tints, i.e., they should, in particular, exhibit cosmetically neutral darkening tones. In addition, these compounds should exhibit rapid lightening with simultaneous good darkening performance and good durability.

This object is achieved by the substances characterized in the claims. In particular, photochromic heterocyclically annellated indeno[1,2-h]chromenes having the general formula (I) and indeno[2,1-f] chromenes having the general formula (II) are provided:

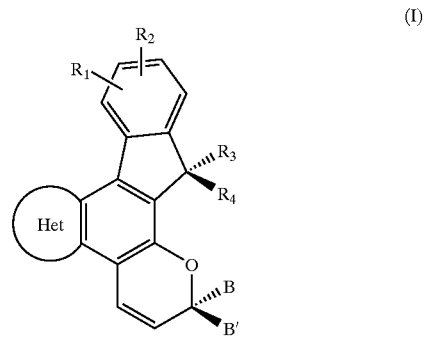

3

-continued

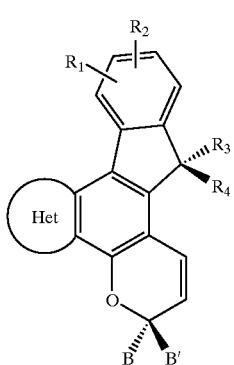

(II)

wherein the groups $R_1$ and $R_2$ independently from each other represent a substituent selected from group A consisting of hydrogen, fluorine, chlorine, bromine, a hydroxy group, a $(C_1-C_6)$ alkyl group, a $(C_1-C_6)$ alkoxy group, a $(C_3-C_7)$ cycloalkyl group which may have one or more heteroatoms, a $(C_1-C_6)$ acyl group, an unsubstituted or monosubstituted phenyl group and an unsubstituted or monosubstituted benzyl group, wherein their substituents are selected from the group consisting of a $(C_1-C_6)$ alkyl group and a $(C_1-C_6)$ alkoxy group;

or the groups $R_1$ and $R_2$ tog ether represent an annellated, unsubstituted, monosubstituted or disubstituted benzo or pyrido ring whose substituents are selected from group A;

group $R_3$ represents a substituent selected from among hydrogen, a $(C_1-C_6)$ alkyl group and —OM, wherein M is a substituent selected from group A;

group $R_4$ is a substituent selected from among hydrogen, a hydroxy group, a $(C_1-C_6)$ alkyl group, a $(C_1-C_6)$ alkoxy group, a $(C_3-C_7)$ cycloalkyl group, a $(C_1-C_6)$ acyl group, a respectively unsubstituted, mono-, di- or trisubstituted phenyl group, benzyl group, naphthyl group, phenanthryl group, pyrenyl group, quinolyl group, isoquinolyl group, benzofuranyl group, thienyl group, benzothienyl group, dibenzofuranyl group, dibenzothienyl group, carbazolyl group or indolyl group, wherein their substituents are selected from group A, a $(C_1-C_6)$-ω-phenylalkyl group and a $(C_1-C_6)$-ω-phenoxyalkyl group, wherein the phenyl ring in the α-position in turn may be part of another photochromic pyran system;

or the groups $R_3$ and $R_4$ including the central spiro carbon atom together represent a saturated and/or unsaturated ring member with 5 to 8 carbon atoms of which maximally one may be substituted by a heteroatom selected from the group consisting of O, S and $NR_5$, wherein group $R_5$ is selected from group A, and wherein at least one aromatic or heteroaromatic ring system is fused to the ring member, wherein the ring system is selected from group E consisting of benzene, naphthalene, phenanthrene, pyridine, quinoline, furan, thiophene, pyrrole, benzofuran, benzothiophene, indole and carbazole, and the ring system may have one or more substituents from group A;

the annellated heterocycle (Het) represents a 5 or 6-membered heteroaromatic ring cycle corresponding to the following general formulas:

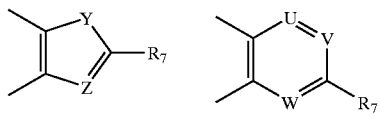

wherein Y is selected from among oxygen, sulfur and $NR_5$, and Z, U, V and W independently from each other are selected from among nitrogen and $CR_6$, wherein groups $R_6$ and $R_7$ independently from each other represent a substituent from group A, or groups $R_6$ and $R_7$ if they are ortho to each other together represent an unsubstituted or monosubstituted benzene ring whose substituents are selected from group A; and B and B' are selected independently from each other from one of the following groups a), b), c) or d), wherein a) they are mono-, di- and trisubstituted aryl groups, wherein the aryl group is phenyl or naphthyl;

b) they are unsubstituted, monosubstituted and disubstituted heteroaryl groups, wherein the heteroaryl group is pyridyl, furanyl, benzofuran-2-yl, benzofuran-3-yl, thien-2-yl, thien-3-yl, benzothien-2-yl, benzothien-3-yl, phenazinyl, phenoxazinyl, phenothiazinyl or julolidinyl;

wherein the substituents of the aryl or heteroaryl groups in a) and b) are those selected from the group consisting of the above-defined group A, hydroxy, amino, mono-$(C_1-C_6)$ alkylamino, di-$(C_1-C_6)$ alkylamino, mono- and diphenylamino which are unsubstituted, monosubstituted or disubstituted on the aromatic, wherein their substituents in turn are selected from group A, pyrrolidinyl, piperidinyl, morpholinyl, thiomorpholinyl, phenazinyl, phenoxazinyl, phenothiazinyl, carbazolyl, unsubstituted, mono- and disubstituted pyrryl, wherein its substituents are selected from group A, c) they are structural units with the following structural formulas (B) and (C):

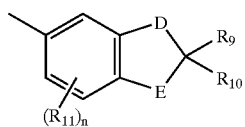

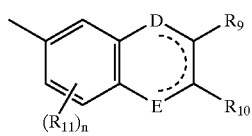

wherein

D and E independently from each other represent oxygen, sulfur, carbon or $NR_8$, wherein the groups $R_8$, $R_9$, $R_{10}$ and $R_{11}$, independently from each other represent a substituent from group A, wherein n represents 1, 2 or 3, provided that, if D is $NR_8$ in formula (B), E represents carbon (i.e., methine (=CH) or methylene ($CH_2$)), or d) B and B' together form an unsubstituted, monosubstituted or disubstituted fluorene-9-ylidene group or a saturated hydrocarbon group, which is $C_3-C_{12}$ spiro-monocyclic, $C_7-C_{12}$ spiro-bicyclic and/or $C_7-C_{12}$ spiro-tricyclic, wherein the fluorene substituents are selected from group A.

The heterocyclically annellated indeno[1,2-h]chromene derivatives according to the invention may be considered heterocyclic relatives of 3H-naphtho[2,1-b]pyrans, and the heterocyclically fused indeno[2,1-f]chromene derivatives according to the invention as heterocyclic relatives of 2H-naphtho[1,2-b]pyrans.

In a preferred embodiment, the annellated heterocycle (Het) is an indole unit, a benzofuryl unit, a benzothienyl, a thienyl unit, a furyl unit, an oxazolyl unit, an imidazolyl unit, a pyrimidinyl unit, a pyrazinyl unit or a triazinyl unit, wherein, in the case of an indole unit, a benzofuryl unit or a benzothienyl unit, annellation to the indenochromene skeleton takes place via the 5-membered heterocycle. Particularly preferably, the annellated heterocycle (Het) is an indole unit, a benzofuryl unit, a benzothienyl, a thienyl unit or a furyl unit.

In one embodiment B and B' independently from each other represent mono-, di- or trisubstituted phenyl groups, wherein the substituents are those selected from the group consisting of the above-defined group A, hydroxy, amino, mono-($C_1$–$C_6$) alkylamino, di-($C_1$–$C_6$) alkylamino, mono- and diphenylamino, which are unsubstituted, monosubstituted or disubstituted on the aromatic, wherein their substituents in turn are selected from group A, pyrrolidinyl, piperidinyl, morpholinyl, thiomorpholinyl, phenazinyl, phenoxazinyl, phenothiazinyl, carbazolyl, unsubstituted, monosubstituted and disubstituted pyrryl, wherein its substituents are selected from group A. In another embodiment B and B' independently from each other represent a julolidinyl group.

Particularly preferred compounds according to the present invention are:

2-(2-fluorophenyl)-2-phenyl-2,14-dihydro-[1]benzofuro[2,3-f]indeno[1,2-h]chromene, 2-(2-fluorophenyl)-2-(4-methoxyphenyl)-2,14-dihydro-[1]benzofuro[2,3-f]indeno[1,2-h]chromene, 2-(2-fluorophenyl)-2-(4-(4-morpholinyl)phenyl)-2,14-dihydro-[1]benzofuro[2,3-f]indeno[1,2-h]chromene, 2-(2-fluorophenyl)-2-phenyl-2,14-dihydro-[1]benzothieno[3,2-f]indeno[1,2-h]chromene 2-(2,4-dimethylphenyl)-2-phenyl-2,14-dihydro-[1]benzothieno[3,2-f]indeno[1,2-h]chromene, 2-(2-fluorophenyl)-2-(4-methoxyphenyl)-2,14-dihydro-[1]benzothieno[3,2-f]indeno[1,2-h]chromene, 2-(2-fluorophenyl)-2-phenyl-2,12-dihydroindeno[1,2-h]thieno[2,3-f] chromene 2-(2-fluorophenyl)-2-phenyl-9-methyl-2,9-dihydro-14H-indeno[1,2-h]indolo[3,2-f]chromene and spiro-9-fluorene-12'-[3,3-diphenyl-3,12-dihydroindeno[2,1-f]-thieno[2,3-h]chromene].

FIG. 1 shows the spectral transmission of a selected compound according to the invention, namely (2-(2-fluorophenyl)-2-(4-methoxyphenyl)-2,14-dihydro-[1]benzofuro[2,3-f]indeno[1,2-h]chromene produced in accordance with Example 2) compared to a corresponding benzo-fused indenochromene compound as described in U.S. Pat. No. 5,869,658.

Figure 2A:
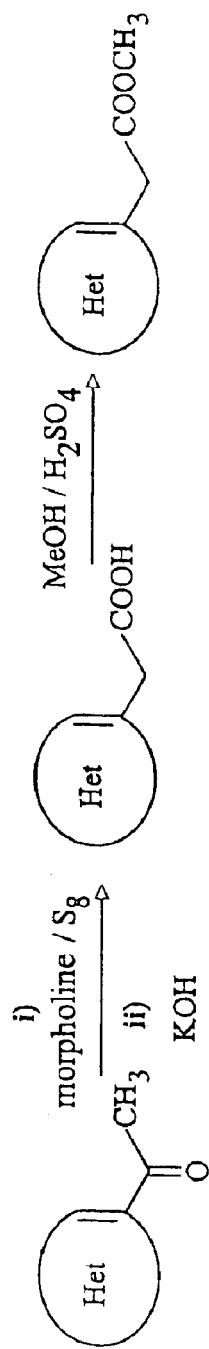
Figure 2A:
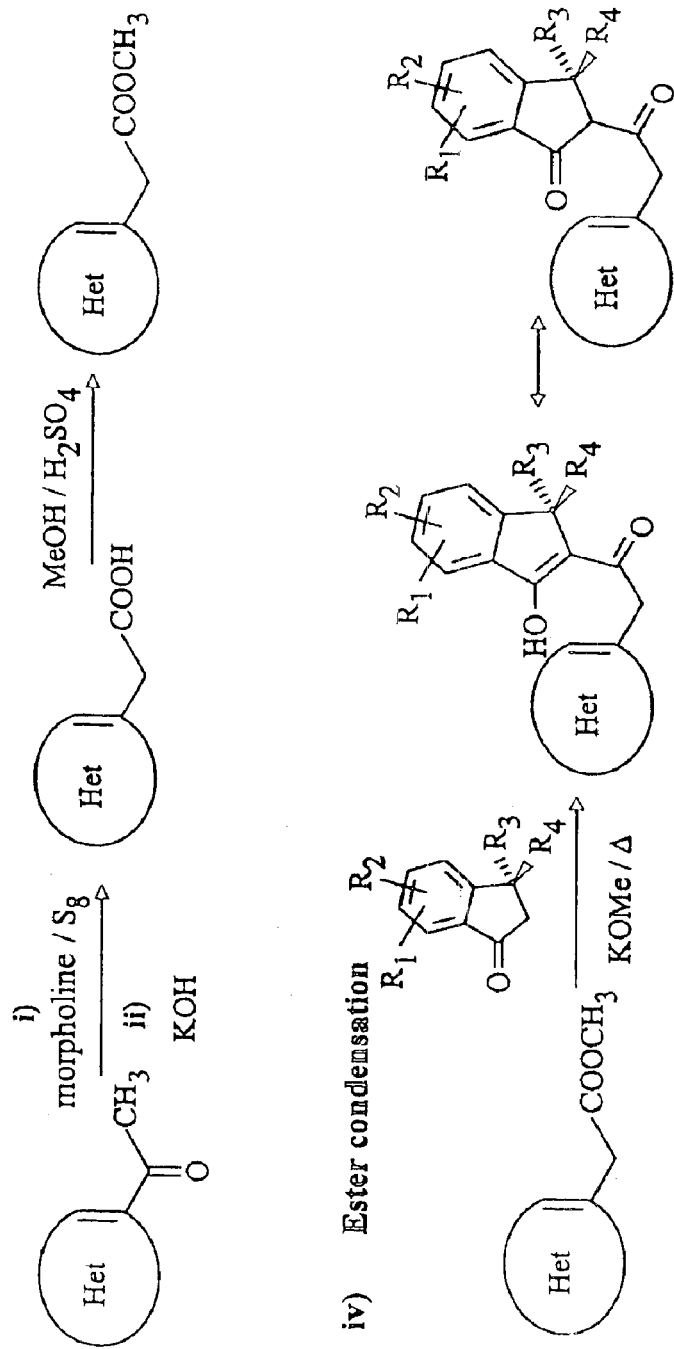
Figure 2B:
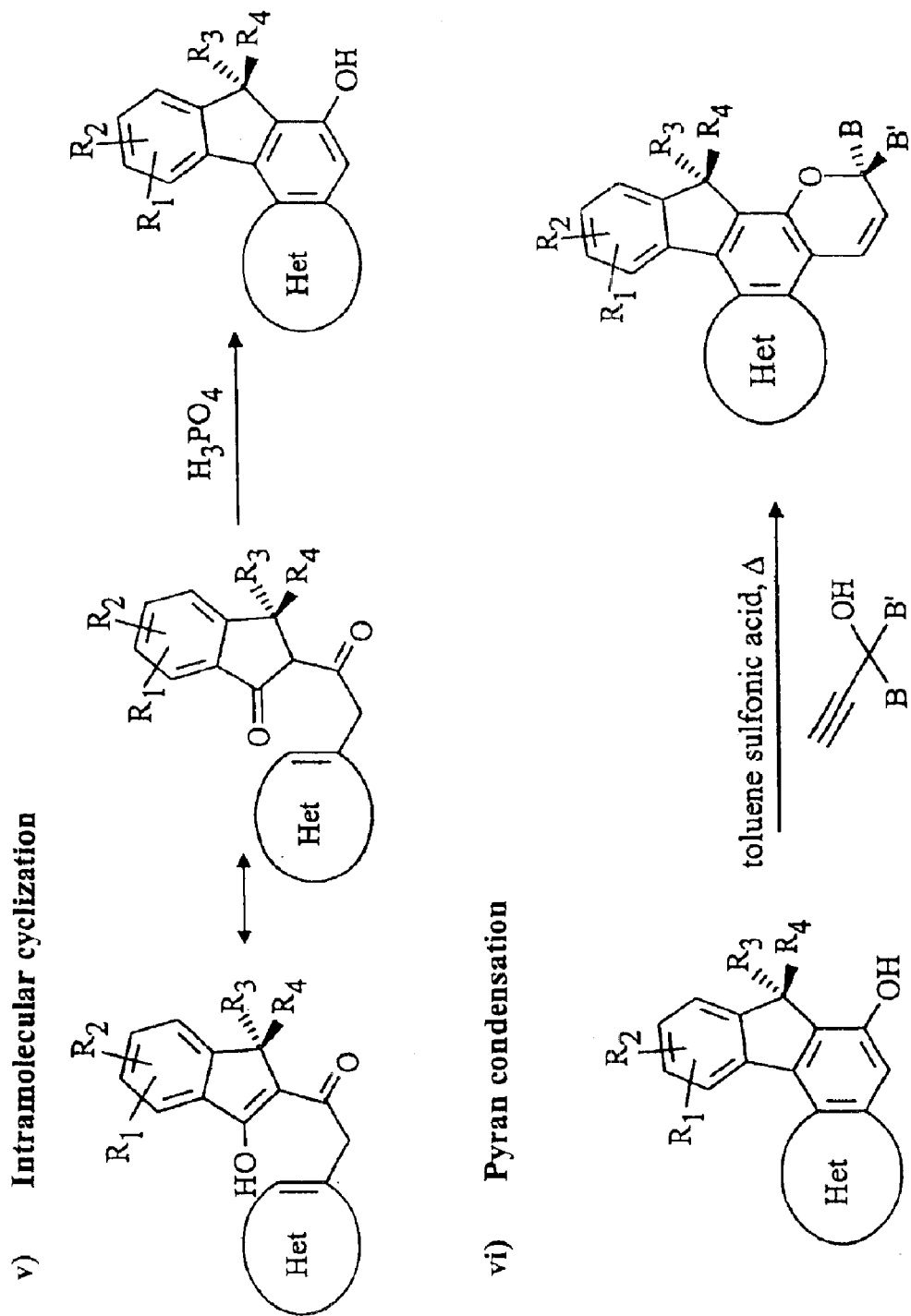

FIGS. 2a and 2b, by way of example, show a reaction scheme for producing photochromic compounds according to the invention.

According to the present invention, photochromic dyes are obtained by specific heterocyclic annellation to indenochromene systems, the photochromic properties of which are significantly improved compared to the compounds available in the prior art.

The properties of the indeno[1,2-h]chromene type (I) compounds will now be described with the aid of a few compounds selected by way of example (cf. Table 1 below). The invention is of course not limited to these embodiments.

Table 1 shows the longest-wave absorption maxima $\lambda_{max}$ in the darkened state, the half-life of the lightening $t_{1/2}$, i.e., the time from the maximum darkening up to a transmission that is equidistant to the maximum darkening and lightening, as well as the UV absorption edge of selected compounds according to the invention.

TABLE 1

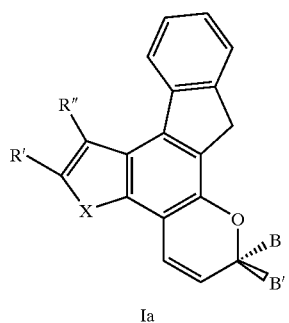

Ia

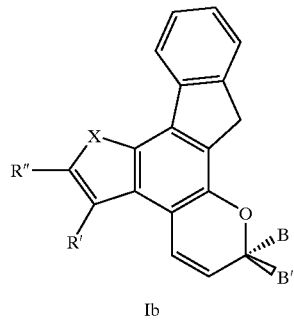

Ib

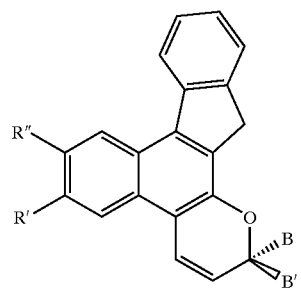

| Example | X | R' | R" | B | B' | Tint darkened | λ_max darkened | $t_{1/2}$ lightening | UV abs. edge |
|---|---|---|---|---|---|---|---|---|---|
| | | Indeno[1,2-h] chromenes of general formula (I) Examples 1 to 8 | | | | | Prior art comparison example (US-A-5,869,658) | | |
| 1 (Ia) | O | benzo | | phenyl | 2-fluoro-phenyl | olive-yellow | 450 nm 590 nm | 3 min | 370 nm |
| 2 (Ia) | O | benzo | | 4-anisyl | 2-fluoro-phenyl | olive-brown | 475 nm 610 nm | 3 min | 370 nm |
| 3 (Ia) | O | benzo | | 4-morpho-linophenyl | 2-fluoro-phenyl | violet | 530 nm 640 nm | 6 min | 370 nm |
| 4 (Ia) | S | benzo | | phenyl | 2-fluoro-phenyl | brown-yellow | 450 nm 550 nm (sh) | 1 min | 400 nm |
| 5 (Ib) | S | benzo | | phenyl | 2,4-xylyl | brown-yellow | 450 nm 550 nm (sh) | 3 min | 400 nm |
| 6 (Ib) | S | benzo | | 4-anisyl | 2-fluoro-phenyl | orange-brown | 475 nm 575 nm (sh) | 1 min | 400 nm |
| 7 (Ib) | S | H | H | phenyl | 2-fluoro-phenyl | brown-yellow | 450 nm 550 nm (sh) | 14 min | 370 nm |
| 8 (Ib) | NMe | benzo | | phenyl | 2,4-xylyl | brown-yellow | 480 nm 590 nm | 30 min | 430 nm (yellow) |
| Comp. Ex. | — | OMe | H | 4-anisyl | 2-fluoro-phenyl | orange | 465 nm | 5 min | 400 nm |

In the longest-wave absorption maxima $\lambda_{max}$ of the compounds according to the invention, two discrete absorption bands are present. The reason for this is the heterocyclic annellation according to the invention of the underlying indenochromene system. In contrast thereto, benzo-fused indenochromene compounds as described in U.S. Pat. No. 5,869,658 have only one absorption band (see spectral comparison in FIG. 1). In addition, the two bands of the compounds according to the invention, in contrast to the benzo-fused indenochromene compounds described in U.S. Pat. No. 5,869,658, are bathochromically shifted (see Examples 2 and 6 according to the invention as compared to the comparison example having identical groups B and B'). This results in a more efficient coverage of the visible spectrum, i.e., greater light attenuation according to the light sensitivity of the human eye $V(\lambda)$. Furthermore, violet to blue-violet darkening tints can be achieved with the compounds according to the invention (see Example 3). In general, dull tints are obtained with the two absorption bands, which is advantageous for achieving cosmetically neutral tints.

With respect to their half-lives $t_{1/2}$, the compounds according to the invention exhibit more rapid lightening than comparable benzo-fused indenochromene compounds as described in U.S. Pat. No. 5,869,658 (see Examples 2 and 6 according to the invention as compared to the comparison example having identical groups B and B'). Particularly rapid lightening occurs in the case of [1]benzothieno[3,2-f]indeno[1,2-h]chromenes (Examples 4–6) of formula type Ib. In these compounds the outer benzene ring of the benzothieno unit, which has a sharp bend in the direction of the photochromic pyran center, interferes with a planar structure of the colored open form of the photochromic compound. This accelerates the reverse reaction of the open form into the closed colorless pyran compound. The difference compared to the compounds of formula type Ia (Examples 1–3 and 7 according to the invention), in which the relatively small heteroatom is located in the direction of the photochromic center and therefore can hardly influence the open form, is significant. An exception to this fact is shown in Example 8 in which the strongly electron donating $H_3C$—N group overcompensates the steric effect. This is also evident in the absorption of the closed form, which clearly absorbs already in the visible spectrum and is therefore strongly pretinted yellow. This characteristic, which is disadvantageous for normal eyeglasses, offers advantages in special cases, e.g., in ski goggles in which the basic yellow tint affords greater contrast, or in glasses for automobile drivers in which the absorption reaching far into the visible spectrum permits good darkening even behind a UV light blocked laminated windshield.

Also important is the position of the UV absorption edges of the compounds according to the invention, i.e., the wavelength below which complete UV absorption takes place. The position of the UV absorption edges of the compounds according to the invention varies as a function of the formula type. The compounds Ib according to the invention in their closed form have a 30 nm longer wave absorption than the corresponding compounds of formula type Ia. Accordingly, when used in eyeglasses, the compounds of formula type Ib offer quasi built-in UV protection up to 400 nm.

The compounds of the indeno[2,1-f]chromene type (II) according to the invention, in contract to the benzo-fused indenochromene compounds described in U.S. Pat. No. 5,869,658, also have two absorption bands. These compounds also show duller tints, so that they may be considered for applications in which cosmetically neutral darkening tints are required.

The compounds according to the invention can be used in plastic materials or plastic objects of any type or form for a wide variety of applications in which photochromic behavior is important. A dye according to the present invention, or a mixture of such dyes, may be used. For example, the photochromic indenochromene dyes according to the present invention may be used in lenses, particularly ophthalmic lenses, lenses for eyeglasses of all types, e.g. ski goggles, sunglasses, motorcycle goggles, visors on protective helmets and the like. Furthermore, the indenochromene dyes can also be used, for instance, for sun protection in vehicles and living spaces in the form of windows, protective shields, covers, roofs or the like.

To produce such photochromic objects, the photochromic indenochromene dyes according to the invention can be applied to or embedded in a polymer material, such as an organic plastic material, using various methods already described in the prior art, as indicated in WO 99/15518.

A distinction is drawn between mass dyeing and surface dyeing techniques. Mass dyeing comprises, for instance dissolving or dispersing the photochromic compound or compounds according to the present invention in a plastic material, e.g. by adding the photochromic compound(s) to a monomer material prior to polymerization. Another way to produce a photochromic object is to permeate the plastic material(s) with the photochromic compound(s) by dipping the plastic material into a hot solution of the photochromic dye(s) according to the present invention or, for instance, by using a thermotransfer method. The photochromic compound(s) can, for instance, also be provided in the form of a separate layer between adjacent layers of the plastic material, e.g., in the form of a polymer film. It is also possible to apply the photochromic compound(s) as a part of a coating to the surface of the plastic material. The term "permeation" should be understood as the migration of the photochromic compound(s) into the plastic material, e.g. by solvent-supported transfer of the photochromic compound(s) into a polymer matrix, vapor phase transfer, or other similar surface diffusion processes. Advantageously, such photochromic objects, e.g. lenses for eyeglasses, may be produced not only by means of conventional mass dyeing, but also by means of surface dyeing. In the latter variant, a surprisingly low migration tendency may be achieved. This is advantageous especially in the following processing steps since—for instance in an antireflection coating, due to the reduced back-diffusion under vacuum—delamination and similar defects can be drastically reduced.

Overall, it is possible using the photochromic indenochromene dyes according to the invention to apply or embed compatible tints, i.e., dyes, to or in the plastic material (compatible from a chemical and tinting perspective) to meet both aesthetic as well as medical or fashion aspects. The specifically selected dye(s) may consequently vary as a function of the intended effects and requirements.

FIGS. 2a and 2b depict general reaction scheme showing, by way of example, the production of the indeno[1,2-h] chromene type (I) compounds according to the invention. Starting from the heterocyclic acetyl compounds the corresponding acetic acid derivatives are obtained by means of Willgerodt-Kindler syntheses in accordance with steps i) and ii). Esterification (in step iii) is followed by ester condensation with 1-indanones (step iv)) and potassium methylate as a base. This produces 2-acyl-1-indanone derivatives, which are used as the starting materials for intramolecular cyclization to form heterocyclically annellated fluorenol derivatives according to step v). These derivatives are finally reacted with 2-propin-1-ol derivatives according to step vi) to obtain the indeno[1,2-h]chromenes of general formula (I).

The heterocyclically annellated indeno[2,1-f]chromene derivatives according to the invention having the general formula (II) may be produced, for instance, analogously to the corresponding benzo-fused spiro fluorenopyrans, as described in EP-A-0 987 260. Instead of using benzophenones as starting materials, benzoyl-substituted heterocycles are used (cf. Example 9).

The production of selective indenochromene derivatives according to the invention will now be described in greater detail by way of example. Of course, these examples should not be construed as limiting the scope of protection of the present invention, but are merely intended for illustration.

EXAMPLES

Example 1 i) A mixture of 2-acetyl-1-benzofuran (32 g) and sulfur (10 g) in 40 ml morpholine was refluxed for 6 h with agitation. After cooling the dark viscous mixture, 50 ml ethanol were added and the mixture was further cooled in an ice bath with agitation. After 10 minutes of agitation a thick suspension was obtained and removed. The solid thus obtained was washed with previously cooled ethanol until the filtrate was colorless. After drying, a curry-colored powder (22 g) was obtained and by means of NMR spectroscopy was identified as 4-(1-benzofuran-2-yl-thioacetyl) morpholine.

ii) The reaction product (22 g) obtained in step i) was added to a mixture of 50 g potassium hydroxide, 50 ml water and 180 ml ethanol. The reaction mixture was refluxed for 6 h with agitation. The ethanol was then distilled off as far as possible. After adding 300 ml water to the residue, the mixture was filtered and the brownish solution was cooled in an ice bath with agitation. The solution was acidified with concentrated hydrochloric acid and the precipitate formed was removed. After washing with water and drying, a yellow solid (12 g) was obtained and was identified by NMR spectroscopy as 1-benzofuran-2-yl-acetic acid.

iii) The reaction product (12 g) obtained in step ii) was refluxed in 200 ml methanol and 1.5 ml concentrated sulfuric acid for 6 h with the exclusion of moisture. The mixture was then poured into 600 ml water and extracted twice with ether. The combined ether phases were successively washed with water and sodium hydrogencarbonate solution. After drying over sodium sulfate and distilling off the solvent, a brownish oil (11 g) was obtained and was identified by NMR spectroscopy as 1-benzofuran-2-yl-methyl acetate.

iv) A mixture of the reaction product (11 g) obtained in step iii), 1-indanone (7 g) and potassium methylate (6 g) in 200 ml absolute toluene was refluxed with the exclusion of moisture for 4 h with agitation. The mixture was allowed to cool, 300 ml water was added, and the two-phase mixture was again heated for 15 min. After cooling, the mixture was transferred to a separatory funnel and the aqueous phase was separated as far as possible. This phase was once more extracted with ether for purification and subsequently acidified with concentrated hydrochloric acid. It was then extracted twice more with ether, and the combined organic phases were successively washed with water and sodium hydrogencarbonate solution. After drying over sodium sulfate and distilling off the solvent, the crude product was purified via a silica gel column (mobile solvent: 3:2 dichloromethane/hexane). The product eluates were combined and the solvent was distilled off. A solid (6 g) was obtained and was identified by NMR spectroscopy as 2-(1-benzofuran-2-ylacetyl)-1-indanone.

v) The reaction product (5 g) obtained in step iv) was suspended in 50 ml orthophosphoric acid and was placed into an oil bath preheated to 100° C. with agitation. After 2 hours at 100° C., a brownish suspension had formed. After cooling, the reaction mixture was poured into 300 ml water with agitation, and the suspension was withdrawn. The precipitate was thoroughly washed with water and dried. A light brown solid (4 g) was obtained and was identified by NMR spectroscopy as 8H-fluoreno[3,4-b][1]benzofuran-7-ol.

vi) 1 g of the reaction product obtained in step v) together with 1-(2-fluorophenyl)-1-phenyl-1-propinol (2 g; produced from 2-fluorobenzophenone and sodium acetylide in DMSO) was suspended in about 100 ml toluene. After adding a spatula-tipful of 4-toluene sulfonic acid, the reaction mixture was refluxed for 15 minutes with agitation. After brief cooling, the toluene was drawn off under vacuum, and the residue was dissolved in 20 ml dichloromethane and subjected to column chromatography with aluminum oxide (water content of 3%) as the stationary and a dichloromethane/hexane mixture (1:2) as the mobile phase. The product eluates were combined and the solvent was distilled off. The residue was digested with a little ether at room temperature, and after brief agitation the suspension was withdrawn. After washing with ether and drying, a slightly beige-colored solid (0.6 g) was obtained and was identified by NMR spectroscopy as 2-(2-fluorophenyl)-2-phenyl-2,14-dihydro-[1]benzofuro[2,3-f]indeno[1,2-h]chromene.

Example 2

The procedure was analogous to Example 1, except that in step vi) the reaction was effected with 1-(2-fluorophenyl)-1-(4-methoxyphenyl)-1-propinol (produced from 2-fluoro-4'-methoxybenzophenone and sodium acetylide in DMSO) instead of with 1-(2-fluorophenyl)-1-phenyl-1-propinol. A slightly beige-colored solid (0.7 g) was obtained and was identified by NMR spectroscopy as 2-(2-fluorophenyl)-2-(4-methoxyphenyl)-2,14-dihydro-[1]benzofuro[2,3-f]indeno[1,2-h]chromene.

Example 3

The procedure was analogous to Example 1 except that in step vi) the reaction was effected with (1-(2-fluorophenyl)-1-(4-(4-morpholinyl)phenyl)-1-propinol (produced from 2-fluoro-4'-(4-morpholinyl) benzophenone and sodium acetylide in DMSO) instead of with 1-(2-fluorophenyl)-1-phenyl-1-propinol. A colorless solid (0.7 g) was obtained and was identified by NMR spectroscopy as 2-(2-fluorophenyl)-2-(4-(4-morpholinyl)phenyl)-2,14-dihydro-[1]benzofuro[2,3-f]indeno-[1,2-h]-chromene.

Example 4

The procedure was analogous to Example 1, except that in step i) the reaction was effected with 3-acetyl-1-benzothiophene instead of with 2-acetyl-1-benzofuran. After step v) 7H-fluoreno[4,3-b][1]benzothiophene-6-ol and after cyclization according to step vi) 2-(2-fluorophenyl)-2-phenyl-2,14-dihydro[1]benzothieno[3,2-f]indeno[1,2-h]chromene in the form of a beige-colored solid (0.5 g) was obtained and identified by NMR spectroscopy.

Example 5

The procedure was analogous to Example 4, except that in step vi) the reaction was effected with 1-(2,4-dimethylphenyl)-1-phenyl-1-propinol (produced from 2,4-dimethylbenzophenone and sodium acetylide in DMSO) instead of with 1-(2-fluorophenyl)1-phenyl-1-propinol. A beige-colored solid (0.7 g) was obtained and was identified by NMR spectroscopy as 2-(2,4-dimethylphenyl)-2-phenyl-2,14-dihydro-[1]benzothieno[3,2-f]indeno[1,2-h]chromene.

Example 6

The procedure was analogous to Example 4, except that in step vi) the reaction was effected with 1-(2-fluorophenyl)-1-(4-methoxyphenyl)-1-propinol (produced from 2-fluoro-4'-methoxybenzo-phenone and sodium acetylide in DMSO) instead of with 1-(2-fluorophenyl)-1-phenyl-1-propinol. A colorless solid (0.4 g) was obtained and was identified by NMR spectroscopy as 2-(2-fluorophenyl)-2-(4-methoxyphenyl)-2,14-dihydro-[1]benzothieno[3,2-f]indeno[1,2-h]chromene.

Example 7

The procedure was analogous to Example 1, except that in step i) the reaction was effected with 2-acetylthiophene instead of with 2-acetyl-1-benzofuran. After step v) 6H-fluoreno[3,4-b]thiophene-5-ol and after cyclization according to step vi) 2-(2-fluorophenyl)-2-phenyl-2,12-dihydroindeno[1,2-h]thieno[2,3-f]chromene was obtained in the form of a brownish solid (0.3 g), which was identified by NMR spectroscopy.

Example 8

The procedure was analogous to Example 1 except that in step i) the reaction was effected with 3-acetyl-1-methylindole instead of with 2-acetyl-1-benzofuran. After step v) 12-methyl-7H-fluoreno[4,3-b]indole-6-ol and after cyclization according to step vi) 2-(2-fluorophenyl)-2-phenyl-9-methyl-2,9-dihydro-14H-indeno[1,2-h]indolo[3,2-f]chromene in the form of a beige-colored solid (0.5 g) was obtained and identified by NMR spectroscopy.

Example 9 i) Potassium-tert-butylate (30 g) was suspended in 600 ml tert-butanol and 2-benzoylthiophene (45 g), and succinic acid dimethyl ester (45 g) was added. The mixture was well agitated and refluxed for 1 hour. Thereafter, potassium-tert-butylate (30 g) and succinic acid dimethyl ester (45 g) was again added and refluxed for 2 hours. After cooling the mixture was hydrolyzed with a total of 2 liters of water and acidified with concentrated hydrochloric acid with agitation. It was subsequently extracted twice with 400 ml portions of ether, and the combined ether phases were washed once with 400 ml water. They were then extracted twice with 500 ml portions of saturated sodium hydrogencarbonate solution. The product in the form of carboxylate was transformed [?] into the liquid phase, which was washed once with 200 ml ether and subsequently acidified with concentrated hydrochloric acid with agitation. Thereafter it was extracted twice with 400 ml portions of ether, and the organic phase was washed once with water. After drying over sodium sulfate, the volatile components were drawn off. A viscous oil (70 g) was obtained and was identified by NMR spectroscopy as 3-methoxycarbonyl-4-phenyl-4-(2-thienyl)-3-butene acid.

ii) The reaction product obtained in step i) was dissolved in a solution of potassium hydroxide (40 g) in about 600 ml water. The reaction solution was refluxed for 3 hours. After cooling it was acidified with concentrated hydrochloric acid with agitation and thorough cooling in an ice bath.

Thereafter, it was extracted twice with 400 ml portions of ethyl acetate. The combined ethyl acetate phases were washed once with water and after drying over sodium sulfate were removed under vacuum. The honey-like reaction product (65 g) was identified by NMR spectroscopy as 3-carboxyl-4-phenyl-4-(2-thienyl)-3-butene acid.

iii) The reaction product obtained in step ii) was dissolved with acetyl chloride (35 g) in 300 ml acetic acid and then refluxed for 2 hours with agitation.

After distilling off the solvent, the residue was dissolved in about 600 ml ethyl acetate while still hot and extracted twice with water. The mixture was then extracted twice with 300 ml portions of 5% sodium carbonate solution. The organic phase was washed once more with water, dried over sodium sulfate and removed. The reaction product obtained was a viscous oil (55 g) identified by NMR spectroscopy as (phenyl-2-thienylmethylene) succinic acid anhydride.

iv) The reaction product obtained in step iii) was dissolved in about 600 ml dichloromethane at room temperature and then cooled in an ice bath. Subsequently, aluminum chloride (35 g) was added in portions with agitation and cooling, and the mixture was allowed to come to room temperature overnight. Thereafter, the reaction mixture was poured into 1 liter ice/water for hydrolysis. The organic phase was separated and washed twice with 500 ml portions of water and subsequently extracted twice with 600 ml 5% sodium hydroxide solution. After washing the combined aqueous-alkaline phases with 250 ml ether, the mixture was acidified with concentrated hydrochloric acid with agitation. It was then extracted twice with 400 ml portions of ethyl acetate, and the organic phase was washed with water, dried over sodium sulfate, and the volatile components were drawn off. Based on NMR spectroscopy the residue (30 g) consisted primarily of 3-(2-thienyl)-indene-1-one-2-acetic acid.

v) The reaction product obtained in step iv) was suspended in about 300 ml acetic anhydride. After adding sodium acetate (20 g), the mixture was refluxed for 3 hours with agitation. During cooling a solid was precipitated. After cooling to room temperature the brownish precipitate was removed and washed with a little acetic anhydride. It was then washed with water and dried at 60° C. An orange-colored solid (15 g) was obtained and was identified by NMR spectroscopy as 4-acetoxy-6H-fluoreno[4,3-b]thiophene-6-one.

vi) The reaction product obtained in step v) was suspended in 400 ml ethanol and mixed with potassium hydroxide (20 g). The reaction mixture was refluxed for 2 hours with stirring. After cooling, about half of the ethanol was removed, and the remaining residue together with 1 liter of water was heated until a solution formed. The solution, still hot, was acidified with concentrated hydrochloric acid with agitation. A suspension was formed, which was cooled to room temperature with agitation. The suspension was removed and washed carefully with water. After drying, a red-violet solid (10 g) was obtained and was identified by NMR spectroscopy as 4-hydroxy-6H-fluoreno[4,3-b]thiophene-6-one.

vii) 3 g of the reaction product obtained in step vi) together with 1,1-diphenyl-1-propinol (4 g, produced from benzophenone and sodium acetylide in DMSO) was suspended in about 300 ml toluene. After adding a spatula tipful of 4-toluene sulfonic acid, the reaction mixture was refluxed for 2 hours. After cooling, the toluene was removed under vacuum, and the residue was dissolved in 40 ml dichloromethane and subjected to column chromatography with aluminum oxide (water content 3%) as the stationary and a dichloromethane/hexane mixture (2:1) as the mobile phase. For final purification, the product was digested in about 100 ml methanol and slightly heated. After cooling, the resulting suspension was removed, washed with methanol and dried. A dark red solid (3 g) was obtained and was identified by NMR spectroscopy as 3,3-diphenyl-3,12-dihydroindeno[2,1-f]thieno[2,3-h]-chromene-12-one.

viii) 2 g of the reaction product obtained in step vii) was dissolved in 50 ml absolute THF with agitation. To this solution 2 equivalents of 2-biphenylyl magnesium bromide (produced from 2-bromobiphenyl and magnesium chips in THF solution) were added dropwise, and the mixture was agitated for 1 hour at room temperature. Subsequently, the mixture was poured into water, acidified with concentrated hydrochloric acid until the phases were clear, and the organic phase was then separated. After extraction with water, drying over sodium sulfate and drawing off the volatile components, a dark brown oil remained and was crystallized by adding methanol. The precipitate was removed and washed with methanol. The resulting brownish solid (1 g) was identified by NMR spectroscopy as 12-(2-biphenylyl)-3,3-diphenyl-3,12-dihydroindeno[2,1-f]thieno[2,3-h]chromene-12-ol.

ix) 1 g of the reaction product obtained in step viii) was cyclized in 30 ml glacial acetic acid while being heated. After adding a drop of hydrochloric acid, the mixture was heated for an additional 5 minutes to boiling, and while hot, water was added until the reaction solution became cloudy. After cooling, the precipitate was removed, washed with water and carefully dried. For final purification, the solid was dissolved in 20 ml dichloromethane and subjected to column chromatography with aluminum oxide (water content 3%) as the stationary phase and a dichloromethane/hexane mixture (2:1) as the mobile phase. After digesting with methanol, removing and drying, a slightly beige-colored (0.4 g) solid was obtained and was identified by NMR spectroscopy as spiro-9-fluorene-12'-[3,3-diphenyl-3,12-dihydroindeno[2,1-f]-thieno[2,3-h]chromene].

Production of Test Specimens 500 ppm of the corresponding photochromic dye was dissolved with agitation at room temperature in the employed monomer (TRANSHADE-150 by Tokuyama; refraction index 1.52). After adding an initiator of the alkylperoxyester type (1.5% by weight), the mixture was degassed twice and filled into a mold comprising a plastic ring and two glass molds. Polymerization was then carried out in accordance with the temperature program recommended by Tokuyama. The glass molds were colored black to enable the photochromic dyes to be incorporated into the matrix in their non-excited state. After polymerization had been completed, the test specimens were tempered for 2 hours at 100° C. The test specimens were round planar disks (without optical effect) with a center thickness of about 2 mm.

Determination of the Kinetic Values and the Longest Wave Absorption Maxima

To determine the bleaching (fade) rates, the test specimens were measured in a PTM II kinetics bench by Zeiss (irradiation with 50 k lux according to DIN EN 1836 Section 6.1.3.1.1). The exposure time was 15 minutes; the bleaching time in the dark 10 min. The temperature of the glass was controlled via a thermostated cuvette. During irradiation and bleaching, the transmission—evaluated based on the light sensitivity of the human eye (V(λ)—was recorded at short time intervals. In addition, the PTM II kinetics bench supplied the UV/VIS spectrum of the darkened test specimens at the end of illumination based on which the longest-wave absorption maxima can be determined.

What is claimed is:

1. A photochromic indenochromene compound corresponding to formula (II):

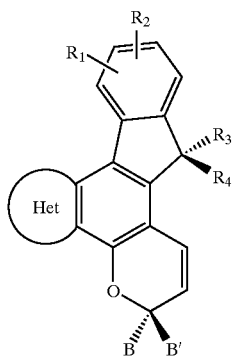

wherein
R₁ and R₂ represent radicals independently selected from the group A, consisting of hydrogen, fluorine, chlorine, bromine, hydroxy, $(C_1-C_6)$-alkyl, $(C_1-C_6)$-alkoxy, $(C_2-C_7)$-cycloaLkyl which may include one or more heteroatoms, $(C_1-C_6)$-acyl, unsubstituted or monosubstituted phenyl, and unsubstituted or monosubstituted benzyl, wherein the phenyl or benzyl substituents are selected from the group consisting of $(C_1-C_6)$-alkyl and $(C_1-C_6)$-alkcoxy; or R₁ and H₂ together represent; an annellated, unsubstituted, monosubstituted or disubstituted benzo or pyrido ring wherein the ring substituents are selected from group A;

R₃ represents a substituent selected from the group consisting of hydrogen, $(C_1-C_6)$-alkyl, and —OM, wherein M is a substituent selected from group A;

R₄ is a substituent selected from the group consisting of hydrogen, hydroxy, $(C_1-C_6)$-alkyl, $(C_1-C_6)$-alkaxy, $(C_3-C_7)$-cycloalkyl, $(C_1-C_6)$-acyl; unsubstituted, monosubstituted, disubstituted or trisubstituted phenyl, benzyl, naphthyl, phenanthryl, pyrenyl, quinolyl, isoquinolyl, benzofuranyl, thienyl, benzothienyl, dibenzofuranyl, dibenzothienyl, carbazolyl and indolyl, wherein the substituents are selected from group A; $(C_1-C_6)$-4-phenylalkyl and $(C_1-C_6)$-4-phenoxyalkyl, wherein the phenyl ring in 4-position in turn may be part of an additional photochromic pyran system; or $R_a$ and R₄ together with the spiro carbon atom represent a saturated and/or unsaturated ring with 5 to 8 carbon atoms, of which at most one may be substituted by a heteroatom selected from the group consisting of O, S and NR₅, wherein R₆ is selected from group A, and wherein at least one aromatic or heteroaromatic ring system selected from group E consisting of benzene, naphthalene, phenanthrene, pyridine, quinoline, furan, thiophene, pyrrole, benzofuran, benzothiophene, indole and carbazole, is annellated to the ring, wherein said ring system may have one or more substituents selected from group A;

the annellated ring (Het) represents a 5 or 6-member heteroaromatic ring corresponding to one of the following formulas:

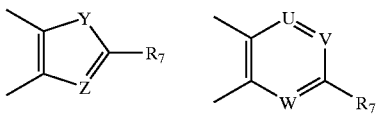

wherein Y is selected from the group consisting of oxygen, sulfur and NR₅, and Z, U, V and W are each independently selected from the group consisting of nitrogen and CR₅, wherein R₆ and R₇ represent substituents independently selected from group A, or R₆ and R₇ if they are ortho to one another together represent an unsubstituted or monosubstituted benzene ring wherein the ring substituents are independently selected from group A; and B and B' are each independently selected from the following groups a), b), c) or d); wherein
group a) consists of monosubstituted, disubstituted and trisubstituted aryl selected from the group consisting of phenyl and naphthyl;
group b) consists of unsubstituted, monosubstituted and disubstituted heteroaryl selected from the group consisting of pyridyl, furanyl, benzofuran-2-yl, benzofuran-3-yl, thien-2-yl, thien-3-yl, benzothien-2-yl, benzothien-3-yl, phenazinyl, phenoxazinyl, phenothiazinyl and julolidinyl, wherein the substituents of the aryl or heteroaryl in groups a) and b) are selected from the group consisting of the above-defined group A, amino, mono-$(C_1-C_6)$-alkylamino, di-$(C_1-C_6)$-alkylamino, monophenylamino and diphenylamino unsubstituted, monosubstituted or disubstituted on the phenyl rings, wherein the phenyl ring substituents in turn are selected from group A, pyrrolidinyl, piperidinyl, morpholinyl, thiomorpholinyl, phenazinyl, phenoxazinyl, phenothiazinyl, carbazolyl, unsubstituted, monosubstituted and disubstituted pyrryl, wherein the pyrryl substituents are selected from group A, group c) consists of structural units with the following structural formulas (B) and (C):

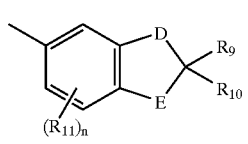

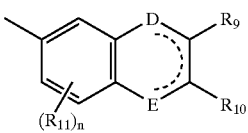

wherein
D and E are independently selected from the group consisting of oxygen, sulfur, carbon or NR₈;
R₈, R₉, R₁₀ and R₁₁ are each independently selected from the group A; and n is 1,2, or 3;
provided that if D represents NR₈ in formula (B), E represent; carbon, or d) B and B' together form an unsubstituted, monosubstituted or disubstituted fluorene-9-ylidene group or a saturated hydrocarbon group, which is $C_3-C_{12}$ spiro monocyclic, $C_7-C_{12}$ spiro bicyclic or $C_7-C_{12}$ spiro tricyclic, wherein the fluorene substituents are selected from group A.

2. A photochromic indenochromene compound according to claim 1, wherein the annellated heterocycle (Het) is selected from the group consisting of indole, benzofuryl, benzothienyl, thienyl, furyl, oxazolyl, imidazolyl, pyrimidinyl, pyrazinyl and triazinyl.

3. A photochromic indenochromene compound according to claim 1, wherein B and B' are each independently selected from monosubstituted, disubstituted or trisubstituted phenyl groups, wherein the phenyl group substituents are selected from the group consisting of group A, amino, mono-($C_1$–$C_6$)-alkylamino, di-($C_1$–$C_6$)-alkylamino, monophenyl- and diphenylamino unsubstituted, monosubstituted or disubstituted on the phenyl ring; wherein the phenyl, ring substituents in turn are selected from group A, pyrrolidinyl, piperidinyl, morpholinyl, thiomorpholinyl, phenazinyl, phenoxazinyl, phenothiazinyl, carbazolyl, unsubstituted, monosubstituted and disubstituted pyrryl, wherein the pyrryl substituents are selected from group A.

4. A photochromic indenochromene compound according to claim 1, wherein B and B' each independently represent a julolidinyl group.

5. A photochromic article comprising a synthetic resin body and at least one photochromic indenochromene compound according to claim 1.

6. A photochromic article according to claim 5, wherein said synthetic resin body is an ophthalmic lens.

* * * * *